US005885270A

United States Patent [19]

Ortiz et al.

[11] Patent Number: 5,885,270
[45] Date of Patent: Mar. 23, 1999

[54] METHOD AND APPARATUS FOR AUTOMATICALLY TRANSFERRING LIQUIDS BETWEEN CONTAINERS

[75] Inventors: Jose A. Ortiz, Telford; Kenneth J. Sylvester, Churchville, both of Pa.

[73] Assignee: Smith Kline Beecham Corporation, Philadelphia, Pa.

[21] Appl. No.: 792,349

[22] Filed: Feb. 5, 1997

[51] Int. Cl.[6] .......... A61B 19/00

[52] U.S. Cl. .......... 604/403; 53/52; 53/505

[58] Field of Search .......... 604/403–407; 53/52, 505, 506, 495, 282; 141/1

[56] References Cited

U.S. PATENT DOCUMENTS

| | | |
|---|---|---|
| 2,530,230 | 11/1950 | Cozzoli . |
| 2,749,688 | 6/1956 | Cozzoli . |
| 2,955,393 | 10/1960 | Müller et al. . |
| 3,599,389 | 8/1971 | Hartman . |
| 3,662,517 | 5/1972 | Tascher et al. . |
| 3,940,909 | 3/1976 | Cioni et al. . |
| 4,628,969 | 12/1986 | Jurgens, Jr. et al. . |
| 4,713,925 | 12/1987 | Kafkis . |
| 4,718,463 | 1/1988 | Jurgens, Jr. et al. . |
| 5,373,684 | 12/1994 | Vacca . |

*Primary Examiner*—John G. Weiss
*Assistant Examiner*—Ki Yong O
*Attorney, Agent, or Firm*—Panitch Schwarze Jacobs & Nadel, P.C.

[57] ABSTRACT

A method and apparatus for automatically transferring a predetermined quantity of a sterile liquid to a vial containing a dry medicament for hydrating the medicament and then transferring the hydrated medicament to a container. To hydrate the medicament, a needle is positioned through a vial septum of the vial and an artificial sensor senses when the needle has been positioned through the vial septum and actuates a pump to transfer a predetermined quantity of sterile liquid into the vial. The needle is then removed from the vial septum and the vial is shaken to mix the liquid and medicament. To transfer the hydrated medicament to a container, another needle is positioned through the vial septum. An artificial sensor senses when the needle has been positioned through the vial septum and actuates the pump to transfer the hydrated medicament to the container.

13 Claims, 9 Drawing Sheets

METHOD AND APPARATUS FOR AUTOMATICALLY TRANSFERRING LIQUIDS BETWEEN CONTAINERS

BACKGROUND OF THE INVENTION

The present invention relates to transferring liquids between containers and, more particularly, to a method and apparatus for automatically hydrating powdered medicaments in vials and transferring the hydrated medicaments within the vials to a container.

Referring now to FIG. 1, in a conventional pharmacy compounding setting, medicaments are often supplied in a dry, powder form within a vial, generally designated 10. Such vials 10 are well understood by those of ordinary skill in the art. Each vial 10 includes a bottom 12 having a periphery 14 and a wall 16 extending generally upwardly from the periphery 14. The container bottom 12 and container wall 16 define an interior container portion 18 which receives the powdered medicament 20. The container wall 16 extends upwardly to form a shoulder 22 and a neck portion 24. The neck portion 24 has an opening which receives a vial septum 26 for sealing the opening and providing access to the interior container portion 18 by piercing the vial septum 26 with a medical needle 28 or spike, such as a hollow transfer or hypodermic needle, in a manner well understood by those of ordinary skill in the art. Many vials 10 include a metallic cap 27 which surrounds and maintains the vial septum 26 in the opening defined by the neck portion 24.

It is the technician's responsibility to reconstitute or hydrate the powdered medicament 20 in the vial 10 and transfer the reconstituted medicament to a sterile IV bag or bottle(not shown in FIG. 1) from which the reconstituted medicament can be dispensed, such as with a syringe. The technician places as many as one to one hundred vials 10 containing the powdered medicament 20 into a laminar flow hood (not shown). A peristaltic pump 30 with first and second sets of transfer tubing 32, 34 and a container 36 of sterile liquid 38, such as water, are also placed under the laminar flow hood. The pump 30 is used to transfer the sterile liquid 38 from the container 36 into the vials 10 for the purpose of reconstituting the powdered medicament 20. The technician connects the first transfer tubing set 32 between the pump 30 and the container of sterile liquid 36. For instance, where the container 36 of sterile liquid 38 is an IV bag, the spike end 32*a* of the first transfer tubing set 32 is connected to the IV bag. The second transfer tubing set 34 extends between the pump 30 and a Luer lock connector 40 to which is attached the transfer needle 28.

To reconstitute the dry, powdered medicament 20 within the vial 10, the technician pierces the vial septum 26 of the vial 10 with the transfer needle 28 and then manually actuates the pump 30 to begin transferring the sterile liquid 38 from the sterile liquid container 36 to the vial 10, as represented by the arrows 38 in the first and second sets of transfer tubing 32, 34. When the pump 30 is actuated, it automatically dispenses a preprogrammed amount of sterile liquid 38 into the vial 10. Once the predetermined amount of sterile liquid 38 is transferred to the vial 10, the pump 30 automatically ceases operation. At this point, the technician removes the needle 28 from the vial septum 26 and inserts it into another vial septum of a vial (not shown) having dry, powdered medicament therein and manually actuates the pump 30. The vial 10 which has been filled with the predetermined amount of sterile liquid 38 is then shaken to thoroughly mix the powdered medicament 20 and the sterile liquid 38. This process is carried out for each of the required vials until they all have been reconstituted.

As can be seen from the foregoing description, the method of reconstituting the powdered medicament 20 is manually intensive. There is a need in the pharmaceutical compounding industry to reduce the number of steps in reconstituting the powdered medicament 20 to save time and effort in this process.

Once the powdered medicament 20 in the vials 10 has been reconstituted, it is then necessary to transfer the reconstituted powdered medicament to an IV bag or vacuum bottle for dispensing the reconstituted medicament to a patient, either through a syringe or infusion vial.

FIG. 2 shows the conventional, manually intensive, process of transferring reconstituted powdered medicament 42 from each of the vials 10 to an empty sterile container 44, such as an IV bag or vacuum bottle. First the pharmacy compounding technician must place a selected number of vials 10, the first and second sets of transfer tubing 32, 34, the pump 30 and an empty container 44 under the laminar flow hood (not shown) for the transfer process. The first set of transfer tubing 32 is then connected between the pump 30 and the empty container 44 by using the spike end 32*a* of the first set of transfer tubing 32 to access the empty container 44. The second set of transfer tubing 34 is connected to the pump 30 and at its distal end includes a Luer lock connector 40 to which the technician attaches a transfer needle 28.

The technician then transfers the reconstituted powdered medicament 42 within each vial 10 to the empty container 44. This process is accomplished by having the technician hold an inverted vial 10 in one hand while the other hand pierces the vial septum 26 with the transfer needle 28. The technician then manually actuates the pump 30 to extract the reconstituted powdered medicament 42 from the vial 10 and the reconstituted powdered medicament 42 flows through the first and second sets of transfer tubing 32, 34 and the pump 30, as represented by the arrows 42. As the reconstituted powdered medicament 42 is being transferred from the vial 10, the technician must be careful to withdraw all of the reconstituted powder medicament 42 and, therefore, must locate the tip of the transfer needle 28 just beyond the inner surface 26*a* of the vial septum 26, as shown in FIG. 2. Once the entirety of the reconstituted powder medicament 42 is withdrawn from the vial 10, the pump 30 either turns off automatically, or the technician must turn the pump 30 off manually. This process is repeated for all required vials until all of the reconstituted powdered medicament 42 has been transferred to one or more empty containers 44. The reconstituted powdered medicament 42 is then transferred from the container 44 directly to a patient or is then transferred to sterile delivery devices, such as syringes.

The foregoing process of transferring the reconstituted powdered medicament 42 to the empty container 44 is also highly labor intensive and takes a significant amount of time for the technician to complete. There is a need in the pharmacy compounding setting to reduce the amount of work necessary to transfer the reconstituted powdered medicament 42 to the empty container 44.

The present invention resulted from the inventors' observations of the foregoing problems and their successful efforts to solve them. With respect to reconstituting the powdered medicaments 20 in the vial 10, the present invention senses when the needle 28 has pierced the vial septum 26 and automatically turns the pump 30 on to transfer the predetermined quantity of sterile liquid 38 to the vial 10. With respect to transferring the reconstituted powdered medicament 42 from the vial 10 to the empty container 44, the present invention provides a vial support station which supports the vial 10 in an inverted position and senses when the vial 10 is located on the support station to automatically actuate the pump 30 and withdraw all of the reconstituted powdered medicament 42 from the vial 10 and transfer it to the empty container 44. Consequently, use of the present invention reduces the steps necessary to reconstitute powdered medicaments which are supplied in vials.

BRIEF SUMMARY OF THE INVENTION

Briefly stated, the present invention is a method of automatically transferring a predetermined quantity of a sterile liquid to a vial containing a dry medicament for hydrating the medicament. Each vial includes a vial septum. The method comprises the steps of positioning a needle through the vial septum; artificially sensing when the needle has been positioned through the vial septum; pumping a predetermined quantity of sterile liquid through the needle into the vial in response to sensing the needle being positioned through the vial septum; and removing the needle from the vial septum.

In another aspect, the present invention is directed to a vial filling system for automatically transferring a predetermined quantity of a sterile liquid to a vial containing a dry medicament for hydrating the medicament. Each vial includes a vial septum. The system comprises a source of sterile liquid. A programmable pump is in fluid communication with the source of sterile liquid for transferring the sterile liquid to a vial. A needle is in fluid communication with the pump for receiving pumped sterile liquid when the needle is positioned through the vial septum. A sensor is in communication with the pump and is positioned proximate the needle for sensing when the needle is positioned through the vial septum. The sensor actuates the pump upon sensing the needle being positioned through the vial septum. The pump transfers a predetermined quantity of sterile liquid through the needle into the vial upon being actuated by the sensor.

Another aspect of the present invention is directed to a method of automatically transferring a liquid within a vial to a container. Each vial includes a vial septum having an inner surface. The method comprises the steps of positioning a needle through the vial septum into the vial; artificially sensing when the needle has been positioned through the vial septum; pumping the liquid through the needle from the vial into the container in response to sensing the needle being positioned through the vial septum; and removing the needle from the vial septum.

Another aspect of the present invention is directed to a liquid transfer system for automatically transferring a liquid within a vial to a container. The system comprises a container for receiving liquid from the vial. A programmable pump is in fluid communication with the container. The system also includes a vial having a liquid therein and a vial septum for accessing the liquid. A vial support station supports the vial as liquid is transferred therefrom. The vial support station includes a base and a vial support member positioned on the base which supports the vial. A needle is located on the base proximate the vial support member. The needle is positioned on the base such that the needle is positioned through the vial septum. The needle is in fluid communication with the pump for transferring liquid in the vial to the container. A sensor is located on the base proximate the needle. The sensor senses when the needle is positioned through the vial septum. The sensor is in communication with the pump and actuates the pump upon sensing the needle being positioned through the vial septum. The pump transfers a predetermined quantity of the sterile liquid through the needle into the vial upon being actuated by the sensor.

BRIEF DESCRIPTION OF THE SEVERAL VIEWS OF THE DRAWINGS

The foregoing summary, as well as the following detailed description of the presently preferred embodiments of the invention, will be better understood when read in conjunction with the appended drawings. For the purpose of illustrating the invention, there is shown in the drawings embodiments which are presently preferred. It should be understood, however, that the present invention is not limited to the particular arrangement and instrumentalities shown. In the drawings.

DETAILED DESCRIPTION OF THE INVENTION

Figure 1:
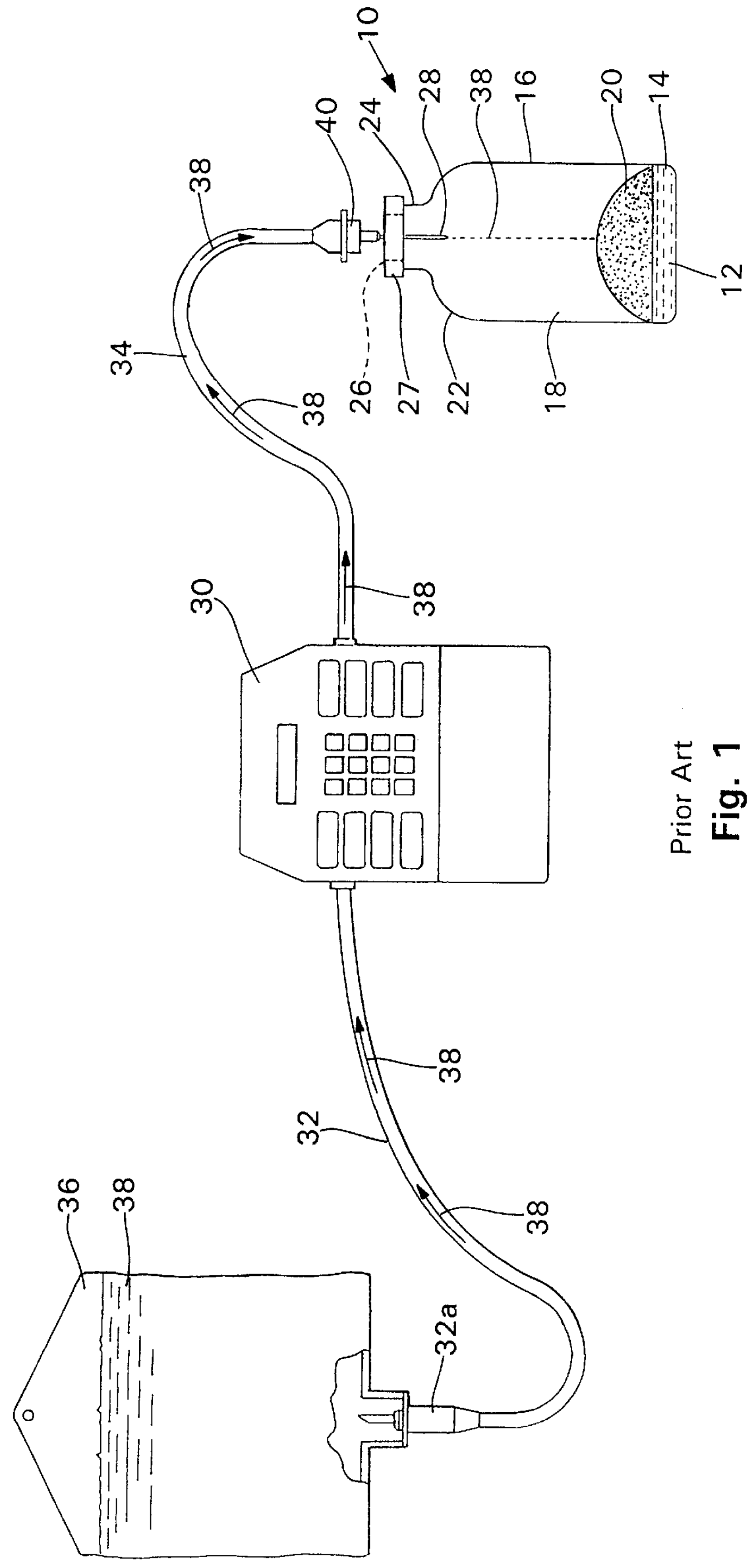
Prior Art Fig. 1
FIG. 1 is a front elevational view, partially in schematic form, of a conventional vial filling system for transferring a predetermined quantity of a sterile liquid to a vial containing a dry medicament.

Certain terminology is used in the following description for convenience only, and is not limiting. The words "right," "left," "lower" and "upper" designate directions in the drawings to which reference is made. The words "inwardly" and "outwardly" refer to directions toward and away from, respectively, the geometric center of the vial filling system or liquid transfer system and designated parts thereof. The terminology includes the words above specifically mentioned, derivatives thereof and words of similar import.

Figure 3:
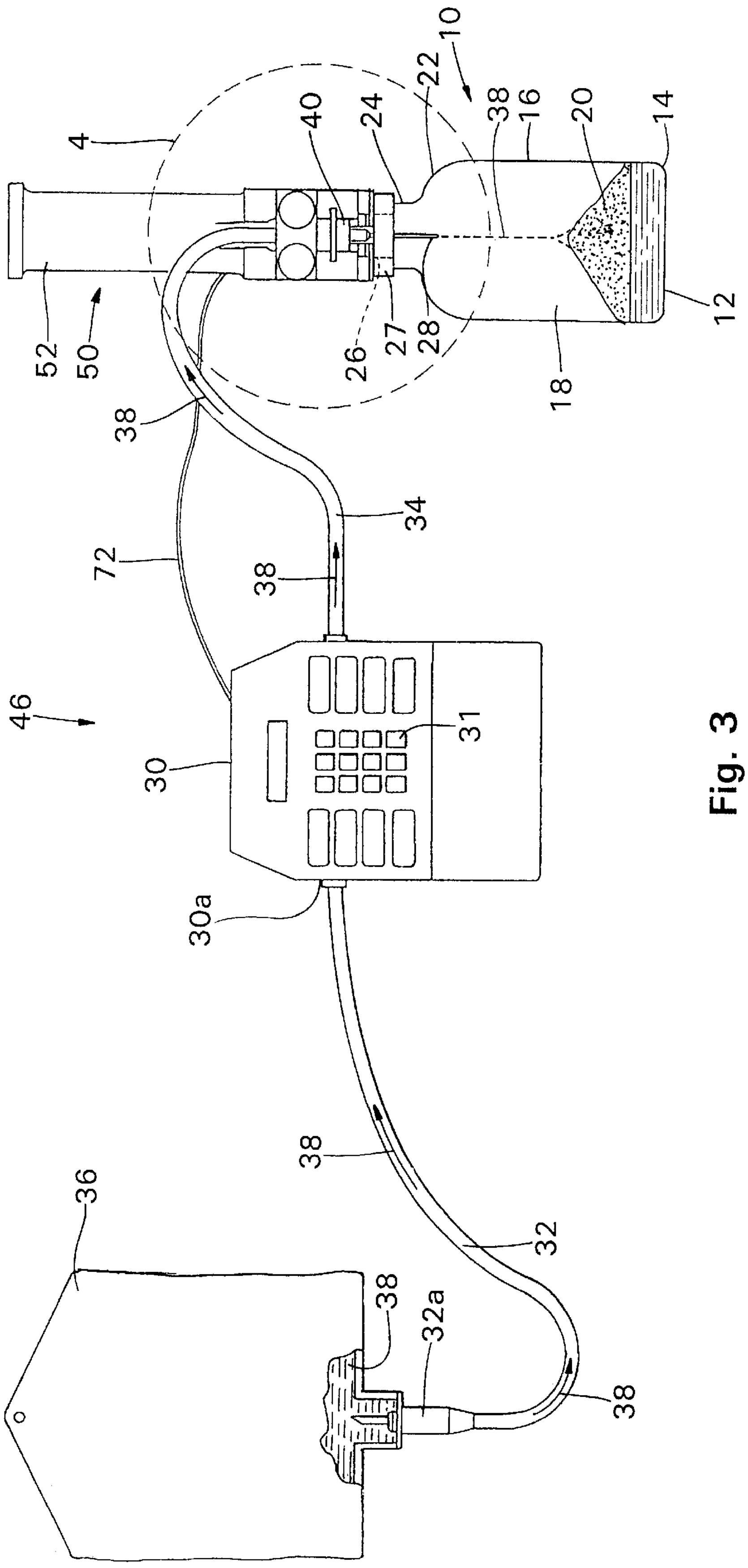
FIG. 3 is a front elevational view, partially in schematic form, of a vial filling system for automatically transferring a predetermined quantity of a sterile liquid to a vial containing a dry medicament in accordance with the first preferred embodiment of the present invention.
Figure 4:
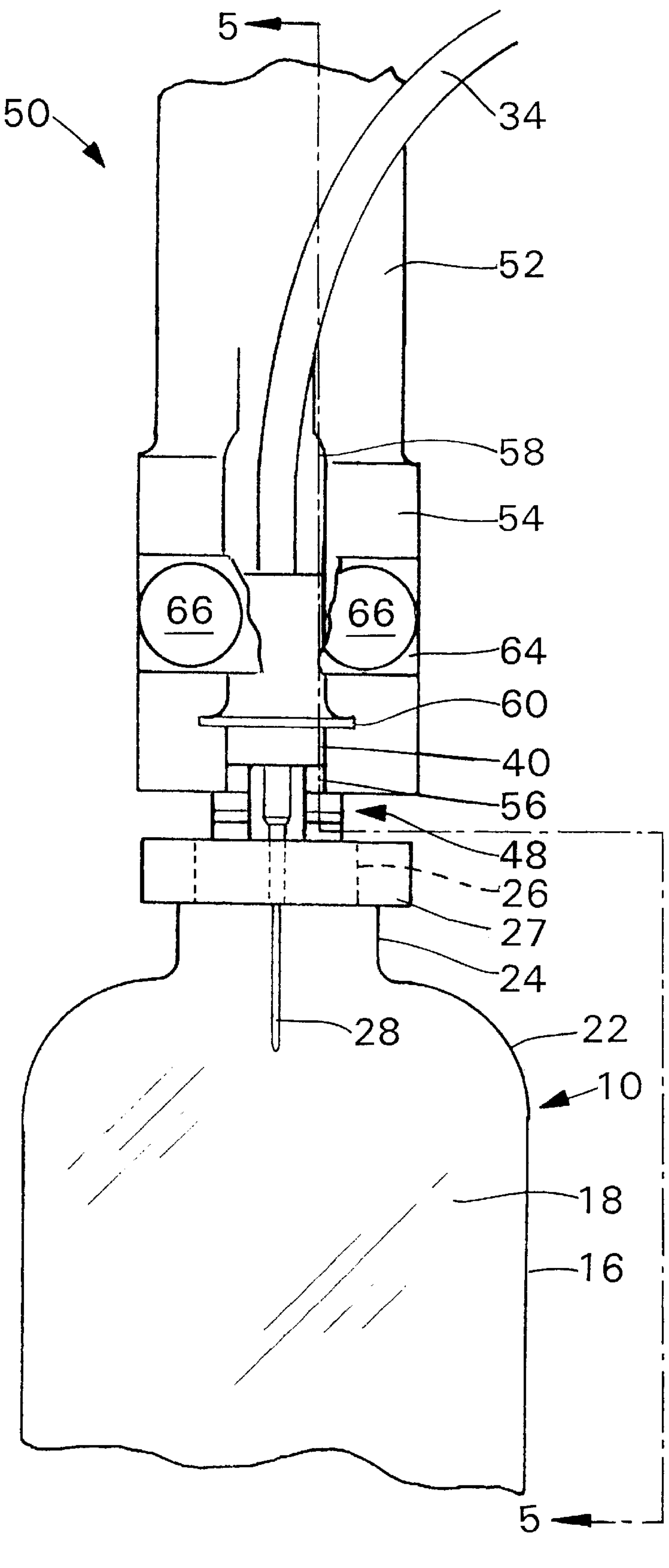
FIG. 4 is a greatly enlarged fragmentary view of a portion of the vial filling system shown in FIG. 3.
Figure 5:
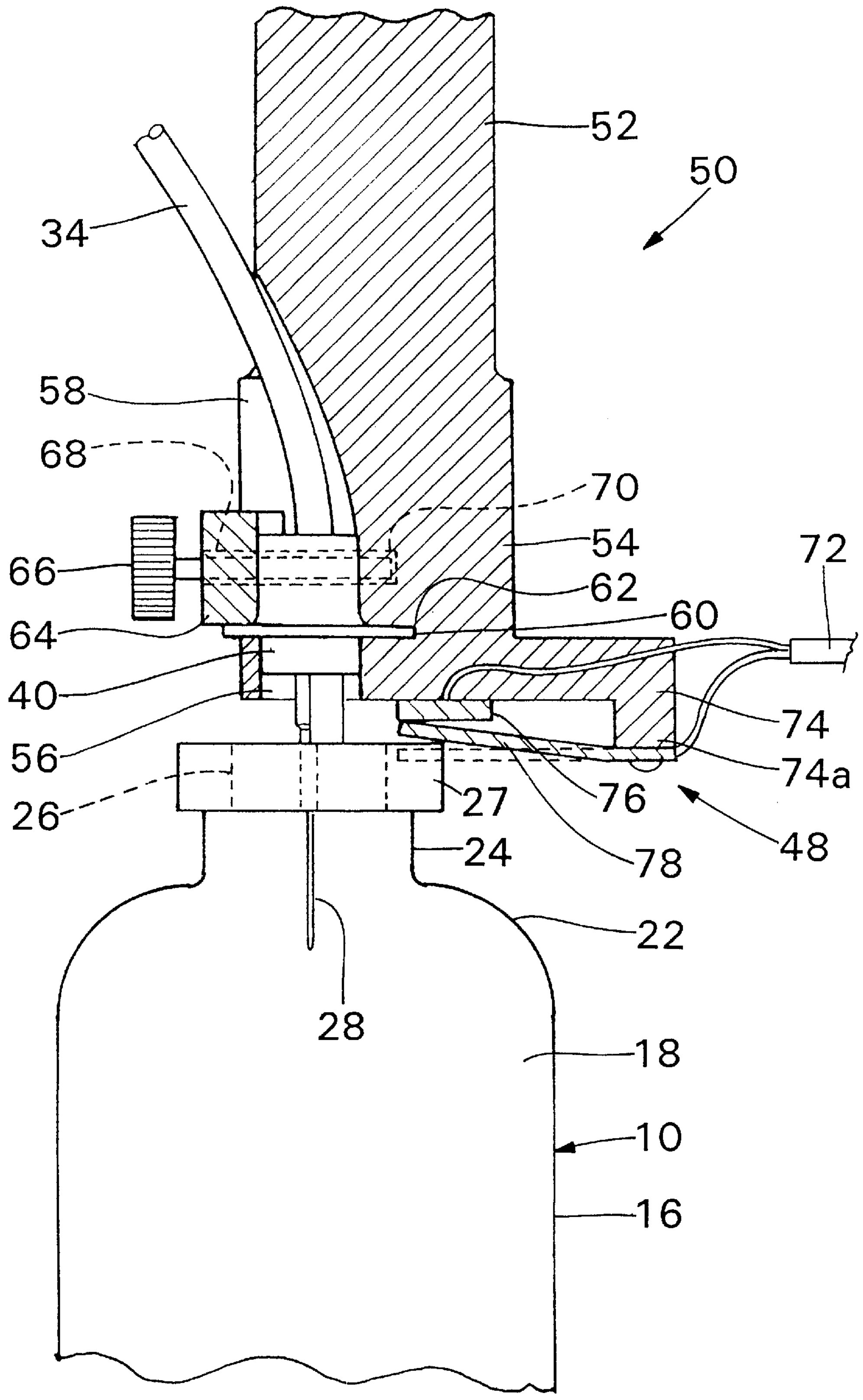
FIG. 5 is a partial cross-sectional view of FIG. 4 taken along lines 5—5 of FIG. 4.

Referring to the drawings in detail, wherein like numerals indicate like elements throughout, there is shown in FIGS. 3 through 5 a vial filling system 46 for automatically transferring a predetermined quantity of a sterile liquid 38 to a vial 10 containing a dry medicament 20 for hydrating or reconstituting the medicament 20. Many of the elements of the vial filling system 46 shown in FIGS. 3 through 5 are the same as the elements used in the conventional process described above in connection with FIG. 1. Accordingly, like numerals indicate the identical elements in FIGS. 1 and 3–5.

In the first preferred embodiment, it is preferred that the dry medicament 20 be a powdered medicament which must be reconstituted or hydrated prior to administering it to a patient. Such dry medicaments are well understood by those of ordinary skill in the art. Accordingly, further description thereof is omitted for purposes of brevity and convenience only, and is not limiting. However, it is also understood by those of ordinary skill in the art that the dry medicament 20 can take other forms. For instance, the dry medicament 20 could be a solid block of material which dissolves when placed in a liquid.

In the first preferred embodiment, it is preferred that the sterile liquid 38 be water. However, it is understood by those of ordinary skill in the art from this disclosure that the present invention is not limited to any particular sterile liquid 38, and that the type of sterile liquid 38 used depends upon the type of dry medicament being hydrated or reconstituted.

Referring now to FIG. 3, the vial filling system 46 includes a source of the sterile liquid 38. The sterile liquid 38 is usually housed within a container 36 which is accessible with a transfer needle, such as an IV bag or vacuum bottle, as is well understood by those of ordinary skill in the art. However, it is also understood by those of ordinary skill in the art that the present invention is not limited to any particular type of container for storing the sterile liquid 38. For instance, the sterile liquid 38 could be housed within a custom bulk container (not shown) which would hold a large volume of the sterile liquid 38 to minimize having to replace the container 36 at frequent intervals.

In the first preferred embodiment, the vial 10 has the same features as the vial 10 described above in connection with FIG. 1. Accordingly, for an understanding of the vial 10 shown in FIG. 3, reference to the foregoing description of FIG. 1 should be made.

As shown in FIG. 3, a programmable pump 30 is in fluid communication with the source or container 36 of sterile liquid 38 for transferring the sterile liquid 38 to the vial 10, in a manner well understood by those of ordinary skill in the art. In the present embodiment, it is preferred that the pump 30 be a programmable pump which can rapidly and accurately transfer a precise quantity of liquid, such as a peristaltic pump. One example of a peristaltic pump which would meet the needs of the present invention is the Baxa Repeater Pump sold by the Baxa Corporation in Englewood, Colo. The pump 30 is programmable using the buttons 31 on the face of the pump 30 in a manner to achieve the functions described hereinafter. While it is preferred that the pump 30 of the present invention be a Baxa Repeater Pump, it is well understood by those of ordinary skill in the art from this disclosure that the present invention is not limited to any particular type of pump, and that other pumps may be used to carry out the functions of the present invention without departing from the spirit and scope of the invention.

The first set of transfer tubing 32 extends between the container 36 and the suction side 30*a* of the pump 30. The first set of transfer tubing 32 connects to the suction side 30*a* of the pump 30 in a manner well understood by those skilled in the art, accordingly, further description thereof is omitted for purposes of brevity and convenience only, and is not limiting. The first set of transfer tubing 32 connects to the container 36 with a conventional spike end 32*a* connection, also well understood by those of ordinary skill in the art.

The needle 28 is in fluid communication with the discharge end 30*b* of the pump 30 for receiving pumped sterile liquid 38 when the needle 28 is positioned through the vial septum 26. More particularly, the second set of transfer tubing 34 has a first end secured to the discharge end 30*b* of the pump 30, in a manner well understood by those skilled in the art. The other end of the second set of transfer tubing 34 includes the Luer lock connector 40 which releasably receives the transfer needle 28, in a manner also well understood by those of ordinary skill in the art.

Referring now to FIGS. 4 and 5, the vial filling system 46 includes a sensor, generally designated 48, which is in communication with the pump 30 and is positioned proximate the needle 28 for sensing when the needle 28 is positioned through the vial septum 26. The sensor 28 actuates the pump 30 upon sensing the needle 28 being positioned through the vial septum 26, as described in more detail hereinafter. Once the pump 30 is actuated by the sensor 48, it transfers a predetermined quantity of sterile liquid 38 from the container 36, through the first set of transfer tubing 32, pump 30, second set of transfer tubing 34, and needle 28 into the vial 10, as schematically represented by the arrows 38. The predetermined quantity of liquid is selected based upon the requirements for reconstituting or hydrating the powdered medicament 20, which will vary depending on the type of powdered medicament 20 being reconstituted or hydrated.

As shown in FIG. 5, the needle 28 and sensor 48 are positioned on a handle 50. The handle 50 includes a gripping portion 52 for being positioned within the hand of the technician or pharmacist. The bottom 54 of the handle 50 includes an aperture 56 which is complementarily sized to receive the Luer lock connector 40. A slot 58 extends upwardly and outwardly from the aperture 56 and accommodates a portion of the second set of transfer tubing 34.

In the first preferred embodiment, it is preferred that the gripping portion 52 be generally cylindrically shaped and sized to fit within the palm of a user. However, it is understood by those of ordinary skill in the art that the present invention is not limited to any specific configuration for the handle 50 or gripping portion 52. For instance, the gripping portion 52 could be ergonomically shaped to include finger indentations and fit within the palm of a user (not shown), without departing from the spirit and scope of the invention.

In the first preferred embodiment, it is preferred that the handle 50, except for the fastening elements described hereinafter, be constructed of a high-strength, lightweight material, such as a polymeric material. However, it is understood by those of ordinary skill in the art that the present invention is not limited to constructing the handle 50 of any particular type of material, and that other materials could be used without departing from the spirit and scope of the invention. For instance, the handle 50 could be constructed of materials which are suitable for sterilization procedures, such as stainless steel.

The needle 28 and Luer lock connector 40 are releasably positioned on the handle 50. That is, the Luer lock connector 40 is releasably positioned within the aperture 56. The Luer lock connector 40 includes a radially extending flange 60 which is located within a complementarily sized slit 62 in the bottom 54 of the handle 50. A locking face plate 64, generally in the form of a parallelepiped, extends across the width of the handle 50 and the Luer lock connector 40 when the Luer lock connector 40 is located within the aperture 56. A pair of lock knobs 66, having threaded bolts 66*a* extending therefrom, secure the locking face plate 64 to the bottom 54 of the handle 50. That is, the threaded bolts 66*a* of each of the lock knobs 66 extend through suitably sized apertures 68 in the locking face plate 64 into threaded holes 70. Thus, the lock knobs 66 are used to secure the locking face plate 64 to the handle 50.

In this manner, it is easy to change the Luer lock connector 40 and transfer needle 28 in the handle 50 by removing the lock knobs 66, and the locking face plate 64. After the locking face plate 64 is removed, the Luer lock connector 40 and needle 28 can be replaced with a new Luer lock connector and needle (not shown). When the new Luer lock connector 40 and transfer needle 28 are in place, the locking face plate 64 is aligned on the face of the handle 50 and the lock knobs 66 are used to threadably secure locking face plate 64 thereto.

While in the present embodiment, it is preferred that the Luer lock connector 40 and transfer needle 28 be releasably secured to the handle 50 using the aperture 56 and locking face plate 64, it is understood by those of ordinary skill in the art from this disclosure that the present invention is not limited to any particular manner of securing the Luer lock connector 40 to the handle 50. For instance, the Luer lock connector 40 could be secured to the handle 50 with a simple interlock mechanism or through the use of suitable hook-and-loop material.

Referring now to FIG. 5, the sensor 48 is positioned on the handle 50 such that upon the needle 28 being positioned through the vial septum 26, the vial 10 contacts the sensor 48. More particularly, the sensor 48 is a switch having an open position (shown in phantom in FIG. 5) and a closed position (shown in solid lines in FIG. 5). The sensor 48 actuates the pump 30 when the switch or sensor 48 is in the closed position via an electrical wire 72 which is in electrical communication with the pump 30. When the sensor or switch 48 is closed, the pump 30 begins pumping fluid from the container 36, through the first set of transfer tubing 32, the pump 30, the second set of transfer tubing 34 and the transfer needle 28 into the vial 10 for a predetermined amount of time which has been preprogrammed into the pump 30.

The bottom 54 of the handle 50 includes an L-shaped flange 74 extending therefrom. The sensor 48 includes a first contact 76 which is secured to the bottom 54 of the handle 50 in a location such that when the needle 28 is disposed through the vial septum 26, the vial septum 26 at least partially overlaps the first contact 76. A second contact 78 extends from the distal end 74*a* of the L-shaped flange 74 generally horizontally to a position just beneath the first contact 76. The second contact 78 assumes the open position, shown in phantom in FIG. 5, in a relaxed state. However, the second contact 78 is flexible such that upon the transfer needle 28 being positioned through the vial septum 26, the vial septum 26 contacts the second contact 78 and flexes it upwardly into engagement with the first contact 76 to cause the sensor or switch 48 to close, and thereby actuate the pump 30. The first and second contacts 76, 78 are preferably secured to the handle 50 in any suitable manner, such as with a screw or an adhesive, in a manner well understood by those of ordinary skill in the art.

While in the first preferred embodiment the sensor 48 is a switch, it is understood by those of ordinary skill in the art from this disclosure that other sensors could be used to sense when the transfer needle 28 has been positioned through the vial septum 26. For instance, a metal proximity detector (not shown) could be used to sense the proximity of the metal cap 27, without departing from the spirit and scope of the invention. Furthermore, a simple button switch (not shown) could extend downwardly from the bottom 54 of the handle 50, which would be actuated by engagement with the vial septum 26.

To use the vial filling system 46, the technician first obtains a container 36 which is filled with the sterile liquid 38. The first set of transfer tubing 32 is then interconnected between the container 36 and the suction side 30*a* of the pump 30. The second set of transfer tubing 34 is then interconnected between the discharge side 30*b* of the pump 30 and the transfer needle 28. The transfer needle 28 and the Luer lock connector 40 are then positioned within the aperture 56 of the handle 50 and locked therein, using the locking face plate 64 and the lock knobs 66.

When the technician is ready to begin hydrating the dry powdered medicament 20 in the vials 10, he or she grasps the gripping portion 52 of the handle 50, and positions the needle 28 through the vial septum 26 of a vial 10. As the needle 28 pierces the vial septum 26, the second contact 78 contacts the upper surface of the vial septum 26 and is flexed upwardly into engagement with the first contact 76 to close the sensor or switch 48 when the needle 28 has fully pierced the vial septum 26 (as shown in FIG. 5). Upon the sensor or switch 48 being closed, the pump 30 is then actuated to transfer the sterile liquid 38 from the container 36 to the interior container portion 18 of the vial 10.

By using the sensor 48, the handle 50 artificially senses when the needle 28 has been positioned through the vial septum 26. The pump 30 pumps a predetermined quantity of the sterile liquid 38 through the needle 28 into the vial 10 in response to sensing the needle 28 being positioned through the vial septum 26. That is, the pump 30 is pre-programmed to transfer a predetermined amount of sterile liquid 38 from the container 36 to the vial 10 and then automatically shuts off. Once the pump 30 has completed its transfer of the predetermined quantity of sterile liquid 38 from the container 36 to the vial 10, the technician removes the needle 28 from the vial septum 26. The technician then repeats the process until all the vials 10 having dry, powdered medicament 20 therein have been hydrated or reconstituted. All of the foregoing steps of hydrating the dry, powdered medicament 20 within the vials 10 are preferably carried out under a laminar flow hood (not shown) to minimize the risk of transferring microbial contaminants to the medicaments.

Figure 2:
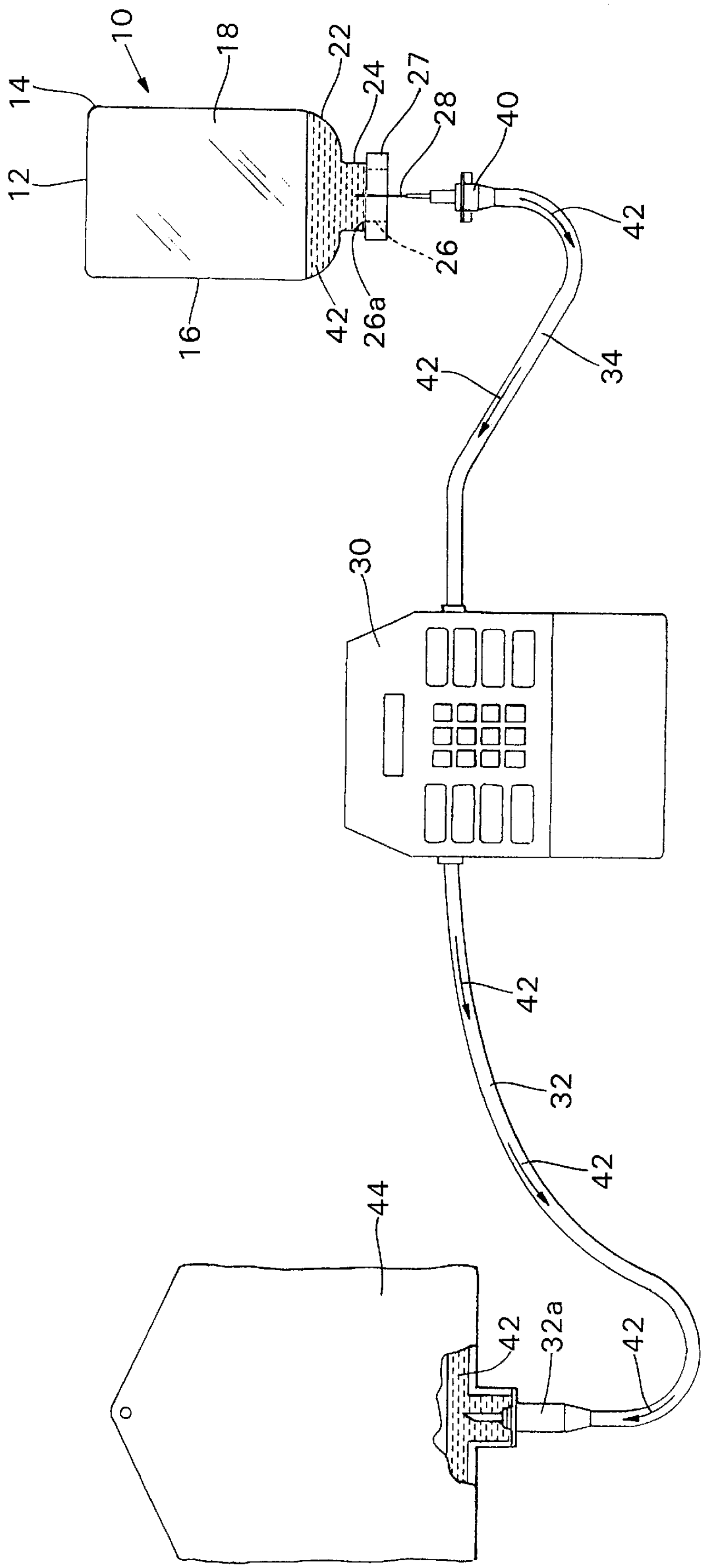
Prior Art Fig. 2
FIG. 2 is a front elevational view, partially in schematic form, of a conventional liquid transfer system for automatically transferring a liquid within a vial to a container.

Referring now to FIGS. 6 through 10, there is shown a liquid transfer system 80 for automatically transferring a liquid, preferably a reconstituted powdered medicament liquid 42, within a vial 10 to a container 44. Many of the elements of the liquid transfer system 80 shown in FIGS. 6 through 10 are the same as the elements used in the conventional process described above in connection with FIG. 2. Accordingly, like numerals indicate the identical elements in FIGS. 2 and 6–10.

Referring now to FIGS. 7 through 10, the liquid transfer system 80 is similar to the vial filling system 46 described above in connection with FIGS. 3 through 5, except that the purpose of the liquid transfer system 80 is to transfer the reconstituted powdered medicament 42 which was created using the vial filling system 46 from each vial to an empty container 44. The liquid transfer system 10 includes a vial support station 82 for supporting the vial 10 as liquid 42 is transferred therefrom. The vial support station 82 includes a base, generally designated 84. The base 84 includes a platform 84*a* which supports the various elements of the vial support station 82. The base 84 further includes a support block 84*b* extending upwardly from the platform 84*a* to also assist in supporting the various elements of the vial support station 82, as described in more detail hereinafter. The platform 84*a* is generally flat and in the form of a parallelogram in plan view.

The support block 84*b*, platform 84*a* and the other elements of the vial support station 82, except for the various fasteners described hereinafter, are constructed of a high-strength, lightweight material, such as a polymeric material. However, it is understood by those of ordinary skill in the art that the present invention is not limited to constructing the platform 84*a*, support block 84*b* and the other elements of the vial support station 82 of any particular material. For instance, stainless steel could be used instead of a polymeric material, without departing from the spirit and scope of the invention.

Figure 7:
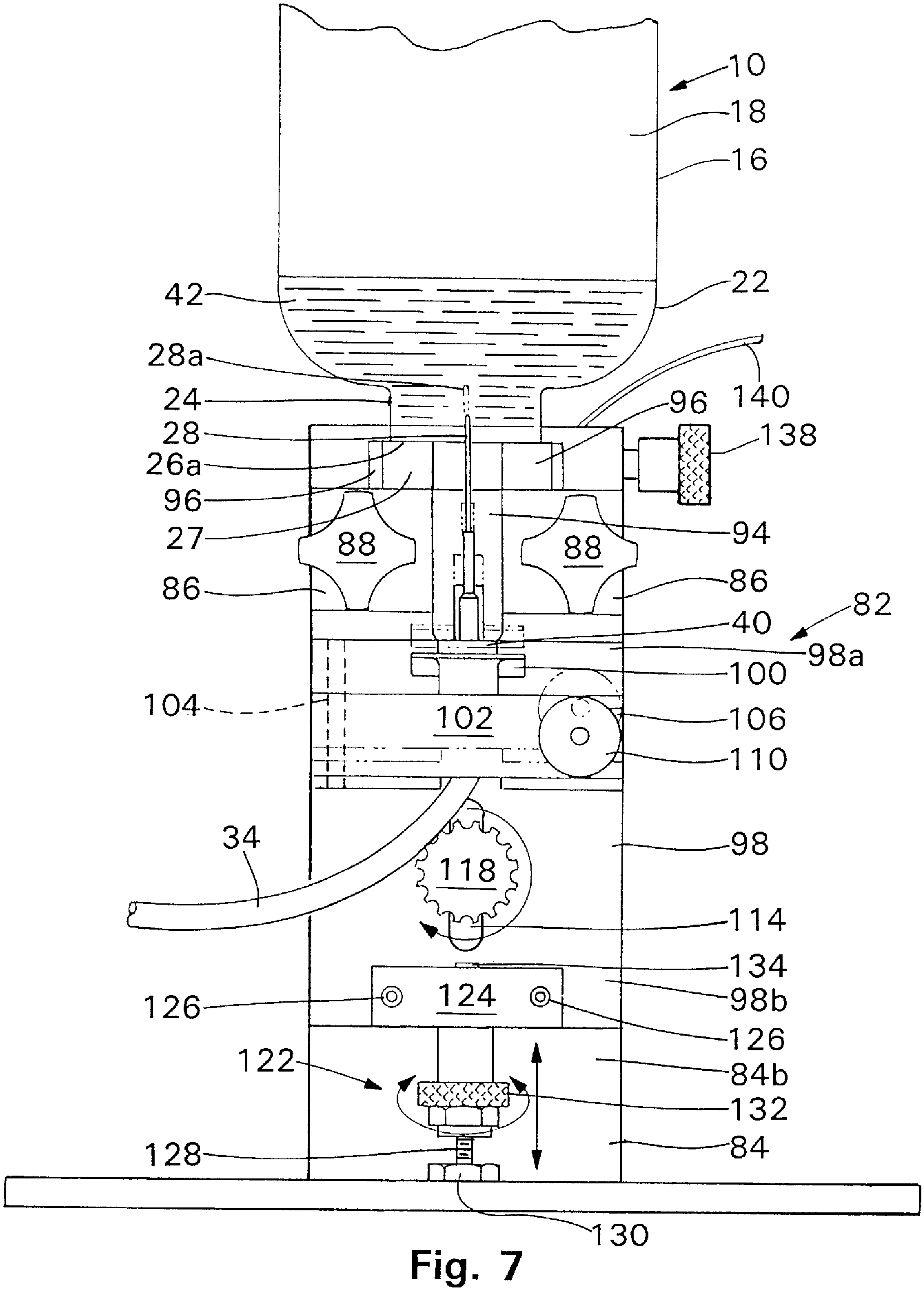
FIG. 7 is a greatly enlarged partial front elevational view of the vial support station shown in FIG. 6.
Figure 8:
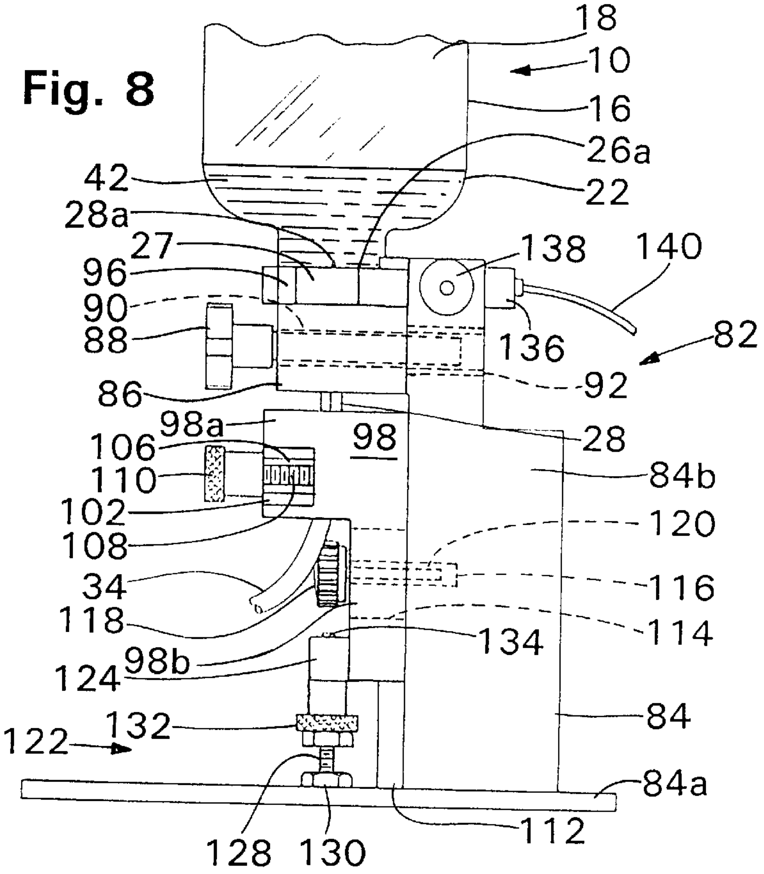
FIG. 8 is a greatly enlarged partial right side elevational view of the vial support station shown in FIG. 6.
Figure 9:
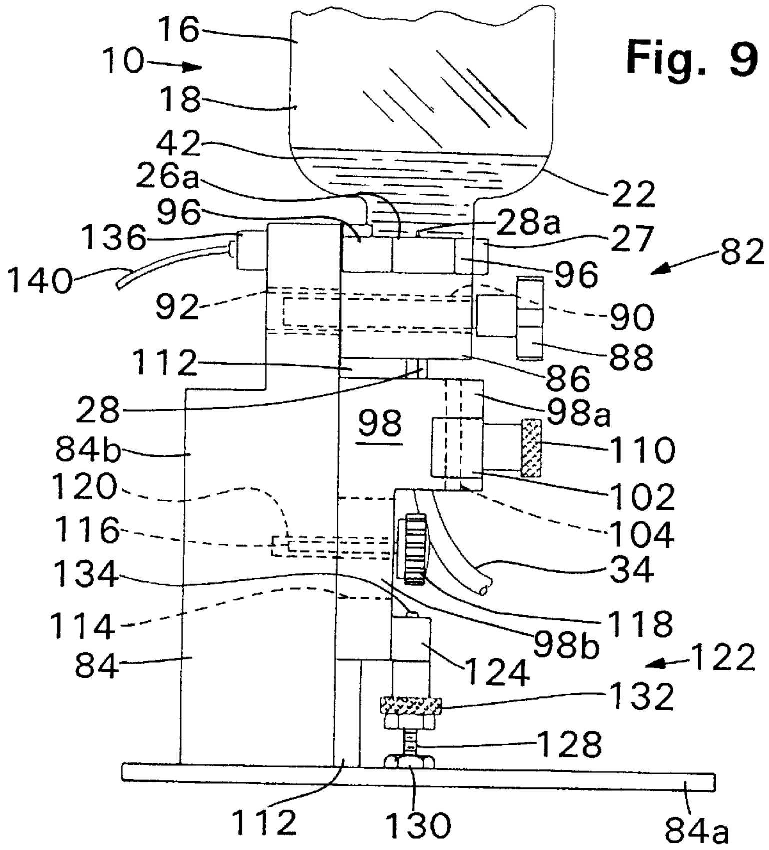
FIG. 9 is a greatly enlarged partial left side elevational view of the vial support station shown in FIG. 6.

Referring now to FIGS. 7–9, a vial support member 86 is positioned on the platform 84*a* of the base 84 and supports the vial 10. In the second preferred embodiment, it is preferred that the vial 10 be located on the vial support member 86 in an inverted position. That is, in the inverted position the vial septum 26 faces downwardly such that all of the reconstituted powdered medicament 42 within the vial 10 flows toward the shoulder 22 and neck portion 24 of the vial 10. The vial support member 86 is secured to the upper end of the support block 84*b* with a pair of threaded knobs 88 which extend through suitably sized holes 90 in the vial support member 86, and are threadably engaged with threaded anchors 92 secured within the upper end of the support block 84*b*. The vial support member 86 includes a slot 94 for allowing the needle 28 to extend through the vial support member 86, as described in more detail hereinafter.

The upper surface of the vial support member 86 receives the top of the vial septum 26 to thereby support the vial 10 on the vial support member 86 in an inverted manner. Several legs 96 extend upwardly from the upper surface of the vial support member 86 and are complementarily positioned to surround and engage the circumferential periphery of the vial septum 26 to assist in supporting the vial 10 on the vial support member 86 in an inverted position.

In the second preferred embodiment, the vial support member 86 is preferably secured to the support block 84*b* using the knobs 88 so that different sized vial support members (not shown) can be secured to the support block 84*b* to allow the vial support station 82 to accommodate different sized vials 10. However, it is understood by those of ordinary skill in the art that the vial support member 86 could be secured to the support block 84*b* in other manners. For instance, the vial support member 86 could be configured as a single integral piece with the support block 84*b* or a dovetail connection could be used (not shown), without departing from the spirit and scope of the invention.

The upper surface of the vial support member 86 and the legs 96 provides sufficient structure to maintain the vial 10 in an inverted position. However, it is understood by those of ordinary skill in the art that the vial support member 86 could be configured in other manners to support the vial 10. For instance, the vial support member 86 could be of tubular construction to complementarily receive the wall 16 of the vial 10. It is also understood by those of ordinary skill in the art that the configuration of the vial 10 may vary, and it would be necessary to modify the shape of the vial support member 86 in order to support a differently shaped vial (not shown) in an inverted position.

Referring now to FIG. 7, the needle 28 is located on the support block 84*b* of the base 84 proximate the vial support member 86. The needle 28 is located on the base 84 such that the needle 28 is positioned through the vial septum 26 when the vial 10 is invertably positioned on the vial support member 86, as shown in FIG. 7. More particularly, the tip of the needle 28 has an opening 28*a* therein. It is preferred that the needle 28 be positioned through the vial septum 26 a distance sufficient such that the opening 28*a* is adjacent an inner surface 26*a* of the vial septum 26 whereby substantially all of the reconstituted powdered medicament liquid 42 is withdrawn from the vial 10 upon actuation of the pump 30.

Referring now to FIGS. 7 through 9, in the second preferred embodiment, the needle 28 is releasably positioned on the base 84 to permit the needle 28 to be replaced as needed. Similarly, the vertical position of the needle 28 on the base 84 is adjustable to accommodate different sized vials 10 to ensure that the needle 28 is positioned through the vial septum 26 a distance sufficient that the opening 28*a* is adjacent the inner surface 26*a* of the vial septum 26.

The needle 28 is releasably secured to a generally L-shaped carriage 98 which is slidably disposed on the support block 84*b*. The carriage 98 includes a horizontal portion 98*a*, to which the needle 28 is releasably secured, and a vertical portion 98*b*. The horizontal portion 98*a* of the carriage 98 includes an aperture 100 which is complementarily sized to received the Luer lock connector 40 having the needle 28 disposed thereon. A securing arm 102 extends horizontally across the face of the horizontal portion 98*a*, as shown in FIG. 7. The securing arm 102 is pivotally mounted at one end via a vertically extending pintle 104. As such, the securing arm 102 is pivotally movable between a closed position, shown in FIGS. 7 through 9, where the securing arm 102 maintains the needle 28 and Luer lock connector 40 within the aperture 100 and an open position (not shown) wherein the securing arm 102 is pivoted away from the aperture 100 to permit removal of the needle 28 and Luer lock connector 40 from the aperture 100. As shown in FIG. 8, the end of the securing arm 102 opposite from the pintle 104 includes a groove 106. A bolt 108 extends from the horizontal portion 98*a* of the carriage 98 through the groove 106 when the securing arm 102 is in the closed position. A knurled nut 110 is threadably secured to the bolt 108, when the securing arm 102 is in the closed position, to maintain the securing arm 102 in the closed position. As such, to move the securing arm 102 to the open position, the knurled nut 110 is unscrewed from the bolt 108 and the securing arm 102 is then permitted to pivot away from the aperture 100 to access the Luer lock connector 40 and needle 28.

While in the present embodiment, it is preferred that the Luer lock connector 40 and needle 28 be secured to the base 84 using the carriage 98 and securing arm 102, it is understood by those of ordinary skill in the art from this disclosure that the present invention is not limited to any particular method of securing the Luer lock connector 40 and needle 28 to the base 84. For instance, the Luer lock connector 40 and needle 28 could be snap fit (not shown) to the base 84, without departing from the spirit and scope of the invention.

Referring now to FIGS. 7, 8 and 9, extending outwardly from the support block 84*b* toward the carriage 98 is a vertically extending rail 112. The vertically extending rail 112 extends upwardly from the platform 84*a* to the bottom surface of the vial support member 86. The vertical portion 98*b* of the carriage 98 includes a vertically extending groove (not shown) which is complementarily sized to receive the rail 112 and permit the carriage 98 to slidably move vertically with respect to the support block 84*b*. The vertical portion 98*b* of the carriage 98 also includes a vertically extending slot 114 (see FIG. 7). A threaded bore 116 is formed in the support block 84*b* in alignment with the slot 114. A knob 118 having a threaded bolt 120 extends through the slot 114 and is threadably secured to the threaded bore 116. When the knob 118 is rotated clockwise, it clamps the carriage 98 to the support block 84*b* to secure the carriage 98 in a fixed vertical position with respect to the support block 84*b*.

A vertical adjustment mechanism 122 extends between the platform 84*a* and the vertical portion 98*b* of the carriage 98. A mounting block 124 extends outwardly from the vertical portion 98*b* of the carriage 98 at its lowermost end. The mounting block 124 is secured to the vertical portion 98*b* of the carriage 98 with suitable fasteners, such as rivets or screws 126. A threaded bolt 128 extends upwardly from the platform 84*a* and is threadably secured to the platform 84*a* and locked in place with a nut 130. A knurled nut 132 is threadably secured to the threaded bolt 128 and includes a push pin 134 extending upwardly therefrom into a suitably sized aperture in the mounting block 124. Rotation of the knurled nut 132 results in vertical translation of the push pin 134 and knurled nut 132 which combine to control the vertical position of the carriage 98, as described below.

The combination of the vertical adjustment mechanism 122 and the knob 118 controls the vertical position of the carriage 98 with respect to the vial support member 86 and secures the carriage 98 to the support block 84*b*. The push pin 134 is slidably disposed within the aperture in the mounting block 124 such that as the knurled nut 132 travels upwardly its engagement with the mounting block 124 controls the vertical position of the carriage 98. As the knurled nut 132 travels downwardly, its engagement with mounting block 124 causes the carriage 98 to slide downwardly along the rail 112 until it engages the knurled nut 132.

To adjust the vertical position of the needle 28, the knob 118 is loosened to permit the carriage 98 to move with respect to the base 84. The knurled nut 132 is the rotated in the desired direction to vertically move the carriage 98. Once the carriage 98 is located at the position which will allow the opening 28*a* in the needle 28 to be located just beyond the inner surface 26*a* of the vial septum 26, the knob 118 is tightened to clamp the carriage 98 in position.

While in the present embodiment it is preferred that the vertical position of the carriage 98 be controlled by the knob 118 and vertical adjustment mechanism 122, it is understood by those of ordinary skill in the art that the position of the carriage 98 can be controlled in other manners, such as with a one-way ratchet mechanism (not shown).

Figure 10:
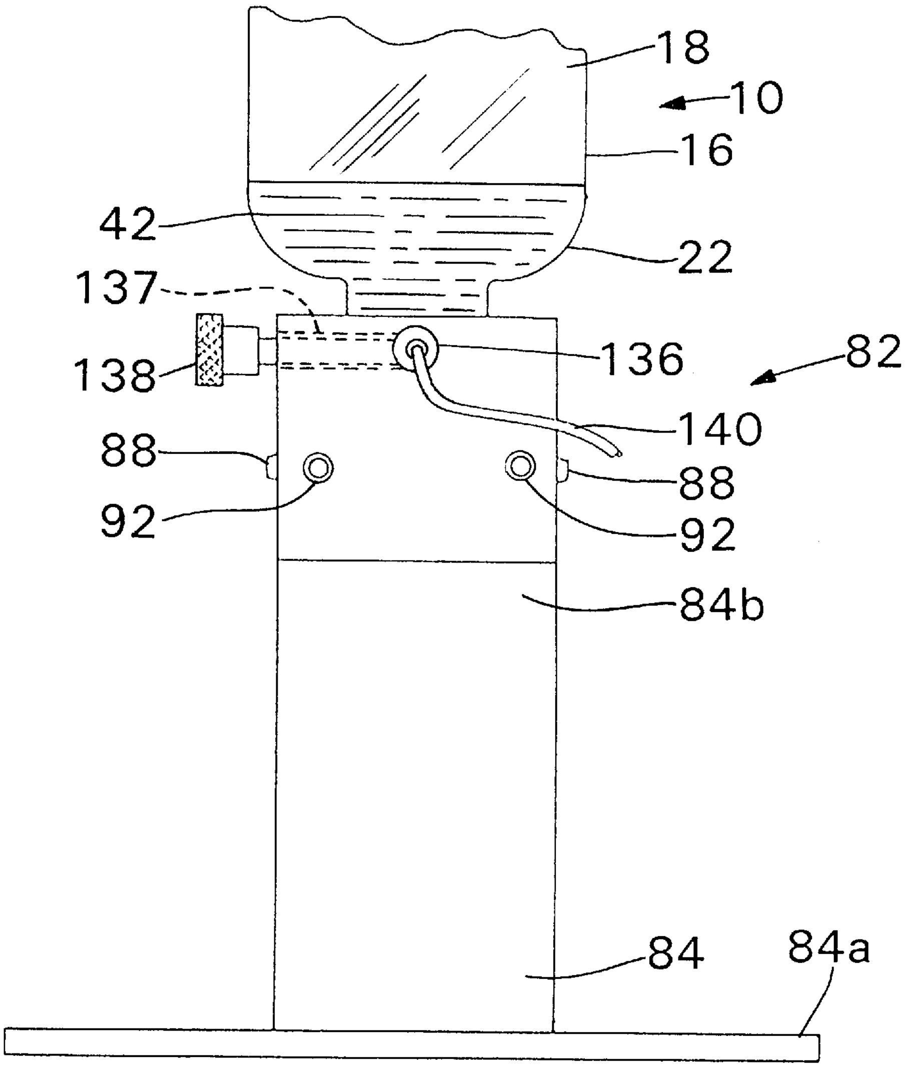
FIG. 10 is a greatly enlarged partial rear elevational view of the vial support station shown in FIG. 6.

Referring now to FIGS. 8 through 10, the vial support station 82 includes a sensor 136 located on the support block 84*b* of the base 84 proximate the needle 28. The sensor 136 senses when the needle 28 is positioned through the vial septum 26 of the vial 10, as described in more detail hereinafter. The sensor 136 is in communication with the pump 30, and actuates the pump 30 upon sensing the needle 28 being positioned through the vial septum 26. The pump 30 transfers a predetermined quantity of the reconstituted powdered medicament 42 through the needle 28 from the vial 10 upon being actuated by the sensor 136.

In the second preferred embodiment; a portion of the vial 10 is constructed of a predetermined material, preferably a metallic material. As mentioned above the cap 27 which surrounds the vial septum 26 of the vial 10 is formed of a metallic material. The sensor 136 is positioned on the support block 84*b* of the base 84 such that upon the needle

28 being positioned through the vial septum 26, the cap 27, which surrounds the vial septum 26 of the vial 10, is positioned proximate the sensor 136. The sensor 136 is responsive to the metallic material being positioned proximate thereto to thereby actuate the pump 30. That is, it is preferred that the sensor 136 be a metal proximity sensor which senses when the metallic cap 27 is located on the upper surface of the vial support member 86.

More particularly, the sensor 136 is generally cylindrically shaped and is positioned through a suitably sized bore in the support block 84*b* at a location such that when the vial 10 is supported by the vial support member 86 the sensing end of the sensor 136 is in close proximity to the cap 27. A set screw 137 having a knurled knob 138 extends generally perpendicularly with respect to the longitudinal axis of the sensor 136 and is threadably mounted within the support block 84*b* to impinge upon the sensor 136 and maintain it within the bore. A wire 140 extends from the sensor 136 and is in communication with the pump 30 to send a signal to the pump 30 when a vial 10 has been positioned on the vial support member 86.

While in the second preferred embodiment, it is preferred that the sensor 136 be a metal proximity detector, it is understood by those of ordinary skill in the art from this disclosure that others sensors could be used to determined when the vial 10 is positioned on the vial support member 86. For instance, a mechanical switch could be used or proximity sensor could also be used without departing from the spirit and scope of the invention.

Figure 6:
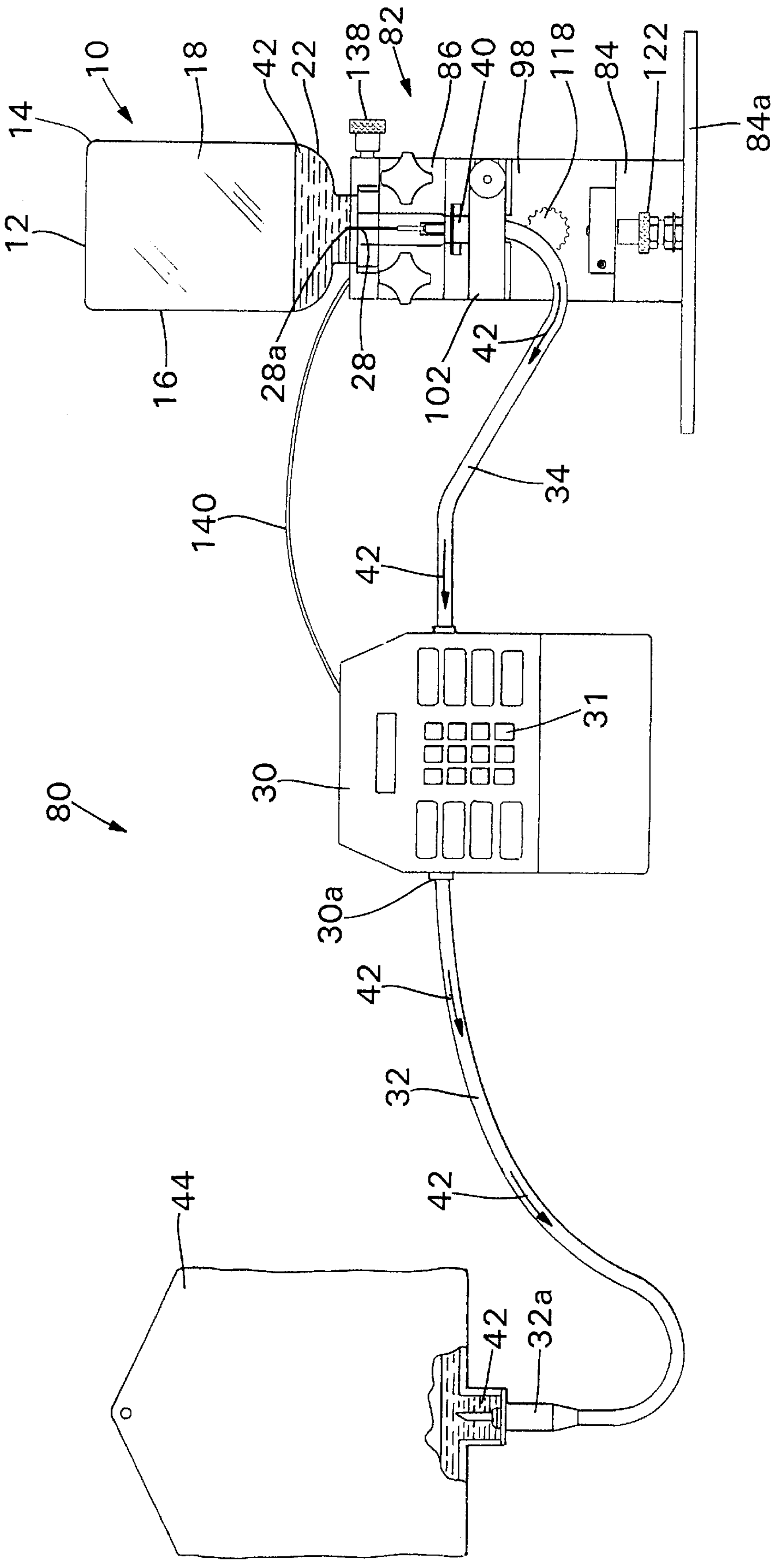
FIG. 6 is a front elevational view, partially in schematic form, of a liquid transfer system for automatically transferring a liquid within a vial to a container in accordance with a second preferred embodiment of the present invention.

Referring now to FIG. 6, to automatically transfer the reconstituted powdered medicament 42 within the vials 10 to an empty container 44, the container 44 is first connected to the suction side 30*a* of the pump 30 using the first set of transfer tubing 32, as described above in connection with the first preferred embodiment. The Luer lock connector 40 and needle 28 are then positioned within the aperture 100 in the horizontal portion 98*a* of the carriage 98 and are secured therein using the securing arm 102 and knurled nut 110. The vertical position of the carriage 98 is then adjusted using the knob 118 and vertical adjustment mechanism 122 such that the opening 28*a* in the needle 28 is located at a vertical position which would place it just beyond the inner surface 26*a* of the vial septum 26 when the vial 10 is positioned on the vial support member 86. Once the vial support station 82 is configured to receive the vials 10, a vial 10 is inverted with the vial septum 26 supported on the vial support member 86 such that the needle 28 is positioned through the vial septum 26 into the vial 10. The sensor 136 then artificially senses the needle 28 has been positioned through the vial septum 26 by sensing the proximity of the metallic cap 27 and actuates the pump 30. The pump 30 then withdraws the reconstituted powdered medicament 42 through the needle 28 from the vial 10 into the container 44 in response to sensing the needle 28 being positioned through the vial septum 26. The pump 30 is programmed to pump for either a predetermined time period which would correspond to the time necessary to empty the contents of the vial 10 or will automatically cease pumping when the vial 10 has been emptied of the reconstituted powdered medicament 42. Once the vial 10 is empty, it is lifted from the vial support station 82 to remove the needle 28 from the vial septum 26. This process is continuously repeated for any number of vials 10 until one or more of the containers 44 are filled with the reconstituted powdered medicament 42.

By following the steps discussed above in connection with FIGS. 3 through 5, and the steps discussed above in connection with FIGS. 6 through 10, the process of reconstituting or hydrating a dry medicament is significantly automated and becomes less labor intensive than the conventional processes described above. For instance, with respect to the first preferred embodiment, the step of having to manually actuate the pump 30 every time a needle 28 pierces the vial septum 26 is obviated. With respect to the second preferred embodiment, the step of having to hold the vial 10 in one hand in an inverted position and insert the needle 28 through the vial septum 26 and then actuate the pump 30 is obviated since the technician merely has to invert the vial 10 onto the vial support station 82 and all of the liquid is automatically withdrawn from the vial 10.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of automatically transferring a liquid within a vial to a container, each vial including a vial septum having an inner surface, the method comprising the steps of:

(a) positioning a needle through the vial septum into the vial;

(b) artificially sensing when said needle has been positioned through the vial septum;

(c) pumping the liquid through said needle from the vial into the container in response to sensing said needle being positioned through the vial septum; and (d) removing said needle from the vial septum.

2. The method as recited in claim 1 wherein in step (a) the vial is in an inverted position as said needle is positioned through the vial septum.

3. The method as recited in claim 1 wherein in step (c) the vial is in an inverted position.

4. The method as recited in claim 3 wherein in step (a) an opening at a tip of said needle is positioned through the vial septum a distance sufficient such that said opening is adjacent the inner surface of the vial septum whereby substantially all of the liquid is withdrawn from the vial in step (c).

5. A liquid transfer system for automatically transferring a liquid within a vial to a container, said system comprising:

(a) a container for receiving liquid from the vial, (b) a programmable pump in fluid communication with the container;

(c) a vial having a liquid therein and a vial septum for accessing said liquid;

(d) a vial support station for supporting said vial as liquid is transferred therefrom, said vial support station comprising:

(1) a base;

(2) a vial support member positioned on said base and supporting said vial;

(3) a needle located on said base proximate said vial support member, said needle being positioned on said base such that said needle is positioned through said vial septum, said needle being in fluid communication with said pump for transferring said liquid in said vial to said container; and (4) a sensor located on said base proximate said needle, said sensor sensing when said needle is positioned through said vial septum, said sensor being in communication with said pump and actuating said pump upon sensing said needle being positioned through said vial septum, said pump transferring a predetermined quantity of said liquid through said needle into said vial upon being actuated by said sensor.

6. The system as recited in claim 5 wherein said vial is located on said vial support member in an inverted position.

7. The system as recited in claim 6 wherein said vial septum has an inner surface and said needle has a tip with an opening therein, said needle being positioned through said vial septum a distance sufficient such that said opening is adjacent said inner surface of said vial septum whereby substantially all of said liquid is withdrawn from said vial upon actuation of said pump.

8. The system as recited in claim 7 wherein said vial has a neck defining an opening for receiving said vial septum and a shoulder extending therefrom, said vial support member engaging said neck and shoulder.

9. The system as recited in claim 5 wherein a portion of said vial is constructed of a predetermined material, said sensor being positioned on said base such that upon said needle being positioned through said vial septum said portion of said vial is positioned proximate said sensor, said sensor being responsive to said predetermined material being positioned proximate thereto to thereby actuate said pump.

10. The system as recited in claim 7 wherein said predetermined material is a metallic material.

11. The system as recited in claim 5 wherein said needle is releasably positioned on said base.

12. The system as recited in claim 5 wherein said position of said needle on said base is adjustable.

13. The system as recited in claim 5 wherein said sensor maintains said pump in a paused condition when said vial is removed from said vial support station.

* * * * *